United States Patent [19]

Coapman

[11] Patent Number: 5,141,961
[45] Date of Patent: Aug. 25, 1992

[54] PROCESS FOR SOLUBILIZING DIFFICULTY SOLUBLE PHARMACEUTICAL ACTIVES

[75] Inventor: Scott D. Coapman, New Haven, Conn.

[73] Assignee: Richrdson-Vicks Inc., Shelton, Conn.

[21] Appl. No.: 722,056

[22] Filed: Jun. 27, 1991

[51] Int. Cl.$^5$ .................. A61K 31/44; A61K 31/40; A61K 31/225; A61K 31/19; A61K 31/135; A61K 31/075

[52] U.S. Cl. .................. 514/629; 514/289; 514/420; 514/343; 514/357; 514/548; 514/570; 514/648; 514/653; 514/718; 514/772

[58] Field of Search .................. 424/80, 456; 514/289, 514/629, 653, 772

[56] References Cited

U.S. PATENT DOCUMENTS

| | | | |
|---|---|---|---|
| 3,851,051 | 11/1974 | Miskel et al. | 424/37 |
| 4,067,960 | 1/1978 | Fadda | 424/14 |
| 4,198,391 | 4/1980 | Grainger | 424/37 |
| 4,690,823 | 9/1987 | Lohrer et al. | 424/456 |
| 4,744,988 | 5/1988 | Brox | 424/456 |
| 4,764,378 | 8/1988 | Keith et al. | 424/435 |
| 4,780,316 | 10/1988 | Brox | 424/456 |
| 4,820,522 | 4/1989 | Radebaugh et al. | 424/468 |
| 4,857,312 | 8/1989 | Hegasy et al. | 424/80 |
| 4,888,239 | 12/1989 | Brox | 428/402.2 |
| 4,968,509 | 11/1990 | Radebaugh et al. | 424/470 |
| 5,006,595 | 4/1991 | Smith et al. | 524/548 |

FOREIGN PATENT DOCUMENTS

| | | |
|---|---|---|
| CA(8):59913b | 10/1982 | Japan . |
| 57-01096J/47 | 10/1982 | Japan . |
| 2185887 | 8/1987 | United Kingdom . |

OTHER PUBLICATIONS

D. Q. M. Craig, "Polyethylene Glycols and Drug Release", Drug Dev. and Industrial Pharmacy, 16(17), pp. 2501-2526 (1990).

J. E. Hilton et al., "The Effect of Wetting Agents on the Dissolution of Indomethacin Solid Dispersion Systems", Int J of Pharm, 31 pp. 157-164, (1986).

L. Lachman et al., "Soft Gelatin Capsules", The Theory and Practice of Industrial Pharmacy, (Lea & Febiger, Phil.) pp. 398-412 (1986).

H. Seager, "Soft Gelatin Capsules: A Solution to Many Tableting Problems", Pharmaceutical Technology, Sep. 1985.

RP Sherer Technical Data Bulletin, "Scherersol TM The Best Solution for Better Drug Absorption".

Primary Examiner—Frederick E. Waddell
Assistant Examiner—Kimberly Jordan
Attorney, Agent, or Firm—Anthony D. Sabatelli; David K. Dabbiere; Douglas C. Mohl

[57] ABSTRACT

The present invention relates to a process for solubilizing at least one difficultly soluble pharmaceutical active in a mixture of polyethylene glycol and polyvinylpyrrolidone. The process does not require water as a solvent or the use of a heating step. In further embodiments, the present invention also relates to a process for encapsulating these solubilized pharmaceutical compositions within soft gelatin shells, which are preferably transparent. Both the resulting compositions and their capsules provide an effective means for oral delivery of a wide variety of difficultly soluble pharmaceutical actives.

24 Claims, No Drawings

PROCESS FOR SOLUBILIZING DIFFICULTY SOLUBLE PHARMACEUTICAL ACTIVES

TECHNICAL FIELD

The present invention relates to a process for solubilizing at least one difficulty soluble pharmaceutical active in a mixture of polyethylene glycol and polyvinylpyrrolidone. In further embodiments, the present invention also relates to a process for encapsulating these solubilized pharmaceutical compositions within soft gelatin shells, which are optionally transparent. Both the resulting compositions and their capsules provide an effective means for oral delivery of a wide variety of difficulty soluble pharmaceutical actives.

BACKGROUND OF THE INVENTION

Liquid, and especially concentrated liquid pharmaceutical compositions offer many advantages over solid compositions. Liquids are easy to swallow and provide an excellent vehicle for the uniform delivery of pharmaceutical actives. Liquids provide a rapid onset of pharmacologic action, since the composition does not first have to disintegrate and dissolve in the gastrointestinal tract. Concentrated liquid compositions are ideally suited for encapsulation within a soft gelatin shell, to provide a portable and easy-to-swallow soft, flexible capsule. Encapsulation would also permit the accurate and uniform delivery of a unit dose of a pharmaceutical active, an advantage which becomes especially important when relatively small amounts of an active are to be delivered. Additionally, soft gelatin capsules are aesthetically appealed (especially when filled with a transparent liquid) and can be manufactured in a wide variety of sizes, shapes, and colors.

However, despite these advantages of liquid compositions, it is not always possible to prepare a liquid composition of the desired pharmaceutical active. Many pharmaceutical actives are poorly soluble and therefore require relatively large volumes of solvent for dissolution . Also, the choice of solvents available for use in liquid compositions is limited by safety, compatibility, stability, and economic concerns. Furthermore, the use of large volumes of solvents for solubilizing pharmaceutical actives is undesirable because the resulting solutions would be so dilute as to require impractically large dosages for delivering a therapeutically effective amount of active. It would thus be difficult, if not impossible, to encapsulate such large volumes into only one or two gelatin capsules and yet have them be of a reasonable size for easy swallowing.

One approach to overcoming these solubility problems has been to incorporate water, water-miscible co-solvents, and surfactants into the compositions. See, U.S. Pat. No. 4,794,117, to Corbiere, issued Dec. 27, 1988 which discloses the solubilization of hydrophobic pharmaceuticals in aqueous solutions of polyethylene glycol at controlled pH; U.S. Pat. No. 4,690,823, to Lohner at al, issued Sep. 1, 1987 which discloses the solubilization of ibuprofen in a mixture of polyethylene glycol and a surfactant; U.S. Pat. No. 3,784,684, to Bossert et al., issued Jan. 8, 1974 which discloses the solubilization of a pharmaceutical active in a mixture of polyethylene glycol and an alcohol having 2-8 carbons and 1-3 hydroxy groups; PCT Application No. WO88/02625, to Yu et al., published Apr. 21, 1988 which discloses the solubilization of an ionized or partly-ionized pharmaceutical active in a mixture of water, polyethylene glycol, and polyvinylpyrrolidone; and European Patent Application No. 152,292, to Rogers, published Aug. 21, 1985 which discloses acetaminophen formulations containing polyethylene glycol, an acrylic acid resin, and a surfactant.

In many instances it may not be possible or desirable to incorporate water, water-miscible co-solvents, or surfactants into a pharmaceutical composition. For example, water-miscible co-solvents, such as ethanol, have the disadvantage of being relatively volatile, thereby resulting in concentration changes in the actives over time. Also, these co-solvents may not be compatible with the desired pharmaceutical actives. A more important disadvantage of water and volatile water-miscible co-solvents is that they are incompatible with soft gelatin capsules. Even though it may be possible to prepare soft gelatin capsules containing these solvents, over time the capsules gradually soften and deform, and develop leaks as these solvents dissolve the soft gelatin shell. Thus, it would be highly desirable to develop a solubilization process which does not require the use of water; and in processes where water-miscible co-solvents are used, it would be highly desirable to develop a process in which the water-miscible solvents are ultimately removed from the final compositions.

Previous investigators have attempted to circumvent these incompatibility problems by modifying the composition of the capsule shell. For example, U.S. Pat. No. 3,865,603, to Szymanski et al., issued Feb. 11, 1975 discloses gelatin compositions which are extended with chemically modified fluidity starches; U.S. Pat. No. 2,580,683, to Kreuger, issued Jan. 1, 1952 discloses gelatin compositions modified by the addition of non-hydroscopic water soluble substances; and Japanese Pat. No. 84044096, to Morishita, issued Jan. 26, 1984 discloses gelatin shells modified with tannic acid, and sugar and/or sugar derivatives. However, it may not always be desirable, feasible or economical to modify the soft gelatin shell with such additives. Thus, it would be highly desirable to find a solubilizing system for pharmaceutical actives which would also be compatible with soft gelatin shells.

Many processes for solubilizing pharmaceutical actives employ heat. However, heating the mixture is not always feasible or desirable because of stability concerns and the additional equipment, time, and costs associated with utilizing a heating process. Thus, it would be highly desirable to develop a solubilization process not requiring the use of heat.

The solubilization process of the present invention overcomes the disadvantages of the prior art by not requiring the use of water as a solvent, except for the minor amounts of water normally present in the materials employed and/or which is absorbed from the environment. Thus, the concentrated pharmaceutical compositions of the instant invention are substantially free of water. Importantly, the process of the present invention does not require a heating step.

It is therefore an object of the present invention to provide a process for solubilizing difficulty soluble pharmaceutical actives. Another object of the present invention is to provide a solubilization process which does not require water as a solvent or the use of a heating step. A further object of the present invention is to provide a process for preparing soft gelatin capsules containing a solution of a difficulty soluble pharmaceutical active, in which the soft gelatin shell is optionally transparent. A still further object of the present invention is to provide pharmaceutical compositions containing difficulty soluble pharmaceutical actives. As even further object of the present invention is to provide soft gelatin capsules containing a solution of a difficulty soluble pharmaceutical active, in which the soft gelatin shell is optionally transparent.

These and other objects of this invention will become apparent in light of the following disclosure.

SUMMARY OF THE INVENTION

The present invention relates to a process not requiring the use of heat or surfactants for solubilizing difficulty soluble pharmaceutical actives, comprising the steps of:
(a) combining and mixing until dissolved
  (i) from about 1% to about 40% of at least one difficulty soluble pharmaceutical active,
  (ii) from about 20% to about 70% of a polyethylene glycol,
  (iii) from about 1% to about 28% of a polyvinylpyrrolidone, and
  (iv) from about 1% to about 50% of a solvent selected from the group consisting of monohydric alcohols having from 1 to 4 carbon atoms and mixtures thereof,
wherein the ratio of said polyethylene glycol to said polyvinylpyrrolidone is at least about 2.5:1; and
(b) evaporating said solvent to obtain a composition containing from about 0.1% to about 6% by weight of said solvent and from about 1.25% to about 50% of said difficulty soluble pharmaceutical active.

The present invention also relates to a process for preparing soft gelatin capsules containing a solution of a difficulty soluble pharmaceutical active, and to the compositions and the filled capsules themselves.

All percentages and ratios used herein are by weight and all measurements are at 25° C., unless otherwise indicated.

DETAILED DESCRIPTION OF THE INVENTION

The term "difficulty soluble pharmaceutical active", as used herein, describes an active having a solubility of less than or equal to 1% by weight in water at 25° C. This term is defined to also include the descriptive terms "sparingly soluble"; "slightly soluble"; "very slightly soluble"; "practically insoluble, or insoluble"; and their equivalents as defined in the USP XXII, p.8 (1990), this reference being incorporated herein by reference in its entirety.

The term "substantially free of water", as used herein, describes highly concentrated pharmaceutical compositions which, as initially prepared, do not contain any water, except for the minor amounts of water normally present in the materials employed in their preparation and/or which is gradually absorbed from the environment or the optional gelatin shell; i.e., less than from about 0.1% to about 8% water, preferably less than from about 0.1% to about 6% water, more preferably less than from about 0.1% to about 4% water, and most preferably less than from about 0.1% to about 2% water. The term "as initially prepared", as used herein, is defined to mean the period of time from when the evaporation step is completed to about 5 minutes thereafter.

Concentrated Liquid Pharmaceutical Compositions

The highly concentrated liquid pharmaceutical compositions of the present invention comprise the following essential, as well as optional, components.

Polyethylene Glycol

An essential component of the present compositions is a polyethylene glycol. Polyethylene glycols generally are clear, viscous liquids or white solids which are soluble in water and many organic solvents. These polymers correspond to the general formula:

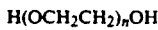

$$H(OCH_2CH_2)_nOH$$

where n is greater than or equal to 4. Polyethylene glycols are described in G. M. Powell, III in *Handbook of Water-Soluble Gums & Resins*, R. L. Division, Ed. (McGraw-Hill, New York, 1980) pp. 18/1-18/31, this reference being incorporated herein by reference in its entirety. Polyethylene glycols, which are also known as "PEGs" or "polyoxyethylenes", are designated by both their average molecular weight range and their average "n" value as in the above designated formula. For example, polyethylene glycol 400, which is also known by the CTFA designation, PEG-8, has an average molecular weight range from 380-420 and an average value of n between 8.2 and 9.1. See *CTFA Cosmetic Ingredient Dictionary*, Third Edition (1982), pp. 201-203; and *The Merck Index*, Tenth Edition, entry 7441, p. 1092 (1983); these two references being incorporated herein by reference in their entirety.

The polyethylene glycols useful herein are those which are liquids at room temperature or have a melting point slightly thereabove. Preferred are the polyethylene glycols having a molecular weight range from about 300 to about 1000 and corresponding n values from about 6 to about 20. More preferred are the polyethylene glycols having a molecular weight range from about 400 to about 1000 and corresponding n values from about 8 to about 20. Most preferred are the polyethylene glycols having a molecular weight range from about 600 to about 1000 and corresponding n values from about 12 to about 20. Most especially preferred is a polyethylene glycol having a molecular weight of about 600 and a corresponding n value of about 12. Moreover, mixtures of two or more polyethylene glycols of different average molecular weight range or n value can also be employed in the present invention. Liquid and low-melting polyethylene glycols are commercially available from Union Carbide (Danbury, Conn.) under the Carbowax ® trademark. See "Carbowax ® Polyethylene Glycols", Union Carbide Technical Bulletin f-4772M-ICD 11/86-20M, this reference being incorporated herein by reference in its entirety.

Polyethylene glycols having an average molecular weight below about 300 are not desirable for use in the instant invention since such polyethylene glycols tend to diffuse into, plasticize, and ultimately disrupt the soft gelatin shells which can be employed to encapsulate the compositions described herein.

The process for preparing the highly concentrated liquid compositions of the present invention comprises adding from about 20% to about 70% polyethylene glycol, more preferably from about 30% to about 60%, and most preferably from about 40% to about 50%.

After the evaporation step, the resulting highly concentrated liquid compositions of the present invention comprise from about 25% to about 87.5% polyethylene glycol, more preferably from about 37.5% to about 75%, and most preferably from about 50% to about 75%.

Polyvinylpyrrolidone

An essential component of the present compositions is polyvinylpyrrolidone ("PVP"), which is a polymer of N-vinyl-2-pyrrolidone having the following formula:

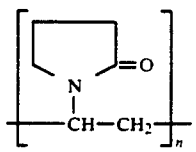

Polyvinylpyrrolidones are described in L. Blecher et al. in *Handbook of Water-Soluble Gums & Resins*, R. L. Davidson, Ed. (McGraw-Hill, New York, 1980) pp. 21/1–21/21, this reference being incorporated herein by reference in its entirety. Polyvinylpyrrolidone has different solubility characteristics based on its polymeric structure. Long-chain polyvinylpyrrolidone, which is also known as povidone, has good solubility in water and a number of organic solvents. Cross-linked polyvinylpyrrolidone, which is also known as crospovidone, is insoluble in virtually all common solvents. Both the soluble and insoluble forms of polyvinylpyrrolidone are commercially available from GAF Chemicals Company (Wayne, N.J.) under the Plasdone® and Polyplasdone® trademarks, respectively, and from BASF Aktiengesellschaft (Ludwigshafen, Germany) under the Kollidon® trademark. Soluble forms of polyvinylpyrrolidone include Plasdone® K-25, Plasdone® K-26/28, Plasdone® K-29/32, Plasdone® C-15, Plasdone® C-30, Plasdone® C-90, Kollidon® 12 PF, Kollidon® 17 PF, Kollidon® 25, Kollidon® 30, and Kollidon® 90. Insoluble forms of polyvinylpyrrolidone include Polyplasdone XL$^R$, Polyplasdone XL$^R$10, Kollidon® CL, and Kollidon® CL-M. See "Tableting With Plasdone®", GAF Technical Bulletin 2302-110R1 (1986); "Polyplasdone XL$^R$, Polyplasdone XL$^R$10", GAF Technical Bulletin 2302-099 R2 (1984); and "Kollidon® Grades, Polyvinylpyrrolidone for the Pharmaceutical Industry", BASF Technical Bulletin MEF 129e, Register 2, May 1986 (Bn); these references being incorporated herein by reference in their entirety.

The soluble forms of polyvinylpyrrolidone are preferred for use in the present invention. Preferred are soluble polyvinylpyrrolidones having an average molecular weight in the range from about 2900 to about 1,100,000; more preferred are those having an average molecular weight in the range from about 9000 to about 45,000; and most preferred are those having an average molecular weight of about 29,000. Moreover, mixtures of two or more soluble polyvinylpyrrolidones of different average molecular weight can be employed.

The process for preparing the highly concentrated liquid compositions of the instant invention comprises adding from about 1% to about 28% of a soluble polyvinylpyrrolidone, more preferably from about 1% to about 10%, and most preferably from about 1% to about 5%.

After the evaporation step, the resulting highly concentrated liquid compositions of the instant invention comprise from about 1.25% to about 35% of a soluble polyvinylpyrrolidone, more preferably from about 1.25% to about 12.5%, and most preferably from about 1.25% to about 6.25%.

An important requirement of the processes and compositions of the instant invention is that the polyethylene glycol component(s) and the polyvinylpyrrolidone component(s) are present in a proper ratio. Preferably, the ratio of the total amount of polyethylene glycol to polyvinylpyrrolidone should be at least about 2.5:1.

Difficulty Soluble Pharmaceutical Actives

The compositions of the instant invention contain at least one difficulty soluble pharmaceutical active as an essential component. In general, these actives have a solubility less than or equal to about 1 percent by weight in water at 25° C. Useful classes of pharmaceutically-active compounds which can be incorporated into the present compositions include analgesics, anti-inflammatory agents, anti-pyretics, calcium channel blockers, beta-blockers, antibacterials, antidepressants, antidiabetics, anti-emetics, antihistamines, cerebral stimulants, sedatives, anti-parasitics, expectorants, diuretics, decongestants, antitussives, muscle relaxants, anit-Parkinsonian agents, bronchodilators, cardiotonics, antibiotics, antivirals, nutritional supplements (such as vitamins, minerals, fatty acids, amino acids, and the like), and mixtures thereof. Difficulty soluble pharmaceutical actives selected from the non-narcotic analgesics/non-steroidal anti-inflammatory drugs are especially useful in the present invention. Examples of such drugs are disclosed in U.S. Pat. No. 4,522,828, to Sunshine et al., issued Jun. 11, 1985; this patent being incorporated herein by reference in its entirety.

Examples of preferred difficulty soluble pharmaceutical actives useful in the present invention include, but are not limited to, acetaminophen, acetylsalicylic acid, ibuprofen, fenbuprofen, fenoprofen, flurbiprofen, indomethacin, ketoprofen, naproxen, their pharmaceutically-acceptable salts, and mixtures thereof. Acetaminophen is especially preferred for use in the compositions of the present invention.

The process for preparing the highly concentrated liquid compositions of the instant invention comprises adding from about 1% to about 40% of a difficulty soluble pharmaceutical active, more preferably from about 15% to about 35%, and most preferably from about 20% to about 30%.

After the evaporation step, the resulting highly concentrated liquid compositions of the instant invention comprise from about 1.25% to about 50% of a difficulty soluble pharmaceutical active, more preferably from about 18.75% to about 43.75%, and most preferably from about 25% to about 37.5%.

Solvents

A solvent selected from the group consisting of the monohydric alcohols having from one to four carbon atoms, and mixtures thereof, is an essential component of the processes of the instant invention. A sufficient quantity of solvent is utilized to aid in the solubilization of the essential components. By "sufficient" is means a quantity of solvent that will ensure solubility of the components of the composition and yet not dilute the composition to the point where it occupies an unreasonably large volume. After mixing and solubilization of the components of the instant invention, the solvent is removed using standard evaporation techniques until the composition is substantially free from solvent. The term "substantially free from solvent" is herein defined to mean that the compositions of the present invention comprise within after about 5 minutes of the evaporation step no more than from about 0.1% to about 6% of solvent after the evaporation step. Ethanol is most preferred as the solvent for use in the processes of the instant invention.

The process for preparing the highly concentrated liquid compositions of the instant invention comprises adding from about 1% to about 50% of solvent, more preferably from about 5% to about 40%, and most preferably from about 10% to about 30%.

After the evaporation step, the resulting highly concentrated liquid compositions of the instant invention comprise no more that from about 0.1% to about 6% solvent.

Additional Pharmaceutical Actives

The compositions of the instant invention can also contain one or more additional pharmaceutical actives having a solubility greater than the difficulty soluble pharmaceutical actives described above. In general, these actives have a solubility greater than about 1 percent by weight in water at 25° C. Useful classes of additional pharmaceutically-active compounds include analgesics, anti-inflammatory agents, antipyretics, calcium channel blockers, beta-blockers, antibacterials, antidepressants, antidiabetics, anti-emetics, antihistamines, cerebral stimulants, sedatives, anti-parasitics, expectorants, diuretics, decongestants, antitussives, muscle relaxants, anti-Parkinsonian agents, bronchodilators, cardiotonics, antibiotics, antivirals, nutritional supplements (such as vitamins, minerals, fatty acids, amino acids, and the like), and mixtures thereof.

Examples of additional pharmaceutical actives useful in the present invention include, but are not limited to, pseudoephedrine and its salts such as pseudoephedrine hydrochloride; dextromethorphan and its salts such as dextromethorphan hydrobromide; doxylamine and its salts such as doxylamine succinate; phenindamine and its salts such as phenindamine hydrogen tartrate; pheniramine and its salts such as pheniramine maleate; chlorpheniramine and its salts such as chlorpheniramine maleate; ephedrine and its salts such as ephedrine sulfate; triprolidine and its salts such as triprolidine hydrochloride; diphenhydramine and it salts such as diphenhydramine hydrochloride, diphenhydramine citrate, and dephenhydramine 8-chlorotheophyllinate; phenyltoxylamine and its salts; guaifenesin; phenylpropanolamine hydrochloride; and mixtures thereof. Preferred additional pharmaceutical actives are dextromethorphan hydrobromide, doxylamine succinate, pseudoephedrine hydrochloride, chlorpheniramine maleate, guaifenesin, triprolidine hydrochloride, diphenydramine hydrochloride and mixtures thereof.

The process for preparing the highly concentrated liquid compositions of the instant invention optionally comprises adding from about 0.5% to about 20% of a second pharmaceutical active, or mixtures thereof.

After the evaporation step, the resulting highly concentrated liquid compositions of the instant invention can optionally comprise from about 0.625% to about 25% of a second pharmaceutical active, or mixtures thereof.

Optional Components

Other components which can be incorporated into the compositions of the instant invention include colorings, flavorings, preservatives, lubricants, flow-enhancers, filling aids, antioxidants, essences, and other aesthetically pleasing components.

Process for Solubilizing Difficulty Soluble Pharmaceutical Actives

The highly concentrated liquid pharmaceutical compositions are prepared using art-recognized principles and methodologies in mixing the ingredients together and in choosing the type of mixing equipment to be used. In a preferred manner of execution, the difficulty soluble pharmaceutical active, polyethylene glycol, polyvinylpyrrolidone, and solvent are combined and mixed until dissolved to form a homogeneous solution. Any optional components can either be added initially or after the essential components are combined.

Next, the solvent is removed from the resulting homogeneous solution until the residual amount of solvent is present at no more than from about 0.1 percent to about 6 percent by weight of the composition. The solvents can be removed using any art-recognized evaporation techniques including, but not limited to, rotary evaporation, spray-drying, flash evaporation, film evaporation, freeze-drying, thin film evaporation, forced circulation evaporation, wiped film evaporation, falling film evaporation, and the like. The resulting solution of the difficulty soluble pharmaceutical active, and any optional components, is substantially free from the added alcoholic solvent, i.e., contains no more than from about 0.1 percent to about 6 percent by weight of solvent. This resulting solution is suitable for encapsulation in a soft gelatin capsule using standard encapsulation techniques.

Soft Gelatin Capsules

Preselected amounts of the highly concentrated liquid pharmaceutical compositions of the present invention can also be encapsulated in a soft gelatin shell. Optionally, the soft gelatin shell is essentially transparent so as to enhance the aesthetic qualities of the capsule. The soft gelatin shells comprise the following essential, as well as optional, components.

Gelatin

Gelatin is an essential component of the soft gelatin shells of the instant invention. The starting gelatin material used in the manufacture of soft capsules is obtained by the partial hydrolysis of collagenous material, such as the skin, white connective tissues, or bones of animals. Gelatin material can be classified as Type A gelatin, which is obtained from the acid-processing of porcine skins and exhibits an isoelectric point between pH 7 and pH 9; and Type B gelatin, which is obtained from the alkaline-processing of bone and animal (bovine) skins and exhibits an isoelectric point between pH 4.7 and pH 5.2. Blends of Type A and Type B gelatins can be used to obtain a gelatin with the requisite viscosity and bloom strength characteristics for capsule manufacture. Gelatin suitable for capsule manufacture is commercially available from the Sigma Chemical Company, St. Louis, Mo. For a general description of gelatin and gelatin-based capsules, see *Remingtons's Pharmaceutical Sciences*, 16th ed., Mack Publishing Company, Easton, Pa. (1980), page 1245 and pages 1576–1582; and U.S. Pat. No. 4,935,243, to Borkan et al., issued Jun. 19, 1990; these two references being incorporated herein by reference in their entirety.

The soft gelatin shell of the capsules of the instant invention, as initially prepared, comprises from about 20% to about 60% gelatin, more preferably from about 25% to about 50% gelatin, and most preferably from about 40% to about 50% gelatin. The gelatin can be of Type A, Type B, or a mixture thereof with bloom numbers ranging from about 60 to about 300.

Plasticizer

A plasticizer is another essential component of the soft gelatin shells of the instant invention. One or more plasticizers is incorporated to produce a soft gelatin shell. The soft gelatin thus obtained has the required flexibility characteristics for use as an encapsulation agent. Useful plasticizers of the present invention include glycerin, sorbitan, sorbitol, or similar low molecular weight polyols, and mixtures thereof.

The shell of the present invention, as initially prepared, comprises from about 10% to about 35% plasticizer, preferably from about 10% to about 25% plasticizer, and most preferably from about 10% to about 20% plasticizer. A preferred plasticizer useful in the present invention is glycerin.

Water

The soft gelatin shells of the instant invention also comprise water as an essential component. Without being limited by theory, the water is believed to aid in the rapid dissolution or rupture of the soft gelatin shell upon contact with the gastrointestinal fluids encountered in the body.

The shell of the present invention, as initially prepared, comprises from about 15% to about 50% water, more preferably from about 25% to about 40% water, and most preferably from about 30% to about 40% water.

Optional Components

Other optional components which can be incorporated into the soft gelatin shells include colorings, flavorings, preservatives, anti-oxidants, essences, and other aesthetically pleasing components.

Soft Gelatin Shell Preparation and Encapsulation

The solubilized pharmaceutical compositions of the present invention can be encapsulated within any conventional soft gelatin shell that is capable of substantially containing the composition for a reasonable period of time. The soft gelatin shells of the instant invention can be prepared by combining appropriate amounts of gelatin, water, plasticizer, and any optional components in a suitable vessel and agitating and/or stirring while heating to about 65° C. until a uniform solution is obtained. This soft gelatin shell preparation can then be used for encapsulating the desired quantity of the solubilized fill composition employing standard encapsulation methodology to produce one-piece, hermetically-sealed, soft gelatin capsules. The gelatin capsules are formed into the desired shape and size so that they can be readily swallowed. The soft gelatin capsules of the instant invention are of a suitable size for easy swallowing and typically contain from about 100 mg to about 2000 mg of the solubilized pharmaceutical active composition. Soft gelatin capsules and encapsulation methods are described in P. K. Wilkinson et al., "Softgels: Manufacturing Considerations", *Drugs and the Pharmaceutical Sciences*, 41 (*Specialized Drug Delivery Systems*), P. Tyle, Ed. (Marcel Dekker, Inc., New York, 1990) pp. 409–449; F. S. Hom et al., "Capsules, Soft" *Encyclopedia of Pharmaceutical Technology*, vol. 2, J. Swarbrick and J. C. Boylan, eds. (Marcel Dekker, Inc., New York, 1990) pp. 269–284; M. S. Patel et al., "Advances in Softgel Formulation Technology", *Manufacturing Chemist*, vol. 60, no. 7, pp. 26–28 (July 1989); M. S. Patel et al., "Softgel Technology", *Manufacturing Chemist*, vol. 60, no. 8, pp. 47–49 (August 1989); R. F. Jimerson, "Softgel (Soft Gelatin Capsule) Update", *Drug Development and Industrial Pharmacy* (*Interphex '86 Conference*), vol. 12, no. 8 & 9, pp. 1133–1144 (1986); and W. R. Ebert, "Soft Elastic Gelatin Capsules: A Unique Dosage Form", *Pharmaceutical Technology*, vol. 1, no. 5, pp. 44–50 (1977); these references are incorporated by reference herein in their entirety. The resulting soft gelatin capsule is soluble in water and in gastrointestinal fluids. Upon swallowing the capsule, the gelatin shell rapidly dissolves or ruptures in the gastrointestinal tract thereby introducing the pharmaceutical actives into the physiological system.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

EXAMPLE I

Solubilized Acetaminophen Composition

A highly concentrated solution containing acetaminophen is prepared from the following ingredients.

| Ingredient | Weight % |
|---|---|
| Acetaminophen | 26.00 |
| Polyethylene Glycol 600 | 52.00 |
| Polyvinylpyrrolidone[1] | 3.00 |
| Ethanol 95% USP | QS 100 |

[1]Available as Plasdone ® K-29/32 from GAF Chemicals Co.

The acetaminophen, polyethylene glycol 600, polyvinylpyrrolidone, and ethanol are combined in a suitable vessel and mixed at room temperature until a homogeneous solution is obtained. Next, the ethanol is removed by rotary evaporation at room temperature. The resulting acetaminophen composition is substantially free from ethanol and water, is suitable for oral administration, and contains about 32.10% acetaminophen, 64.20% polyethylene glycol 600, and about 3.70% polyvinylpyrrolidone.

EXAMPLE II

Soft Gelatin Capsule Containing a Solubilized Acetaminophen Composition

A soft gelatin mixture is first prepared from the following ingredients.

| Ingredient | Weight % |
|---|---|
| Gelatin | 47.00 |
| Glycerin | 15.00 |
| Water | QS 100 | the above ingredients are combined in a suitable vessel and heated with mixing at about 65° C. to form a uniform solution. Using standard encapsulation methodology, the resulting solution is used to prepare soft gelatin capsules containing approximately 1000 mg of the acetaminophen composition of Example I. The resulting soft gelatin acetaminophen capsules are suitable for oral administration.

EXAMPLE III

Solubilized Pharmaceutical Composition

A highly concentrated solution containing acetaminophen in combination with other pharmaceutical actives is prepared from the following ingredients.

| Ingredient | Weight % |
|---|---|
| Acetaminophen | 25.00 |
| Pseudoephedrine Hydrochloride | 3.00 |
| Dextromethorphan Hydrobromide | 1.49 |
| Doxylamine Succinate | 0.38 |
| Polyethylene Glycol 600 | 46.20 |
| Polyvinylpyrrolidone[1] | 2.50 |
| Ethanol 95% USP | QS 100 |

[1]Available as Plasdone ® K-29/32 from GAF Chemicals Co.

The acetaminophen, pseudoephedrine hydrochloride, dextromethorphan hydrobromide, doxylamine succinate, polyethylene glycol 600, polyvinylpyrrolidone, and ethanol are combined in a suitable vessel and mixed at room temperature until a uniform solution is formed. Next, the ethanol is removed by rotary evaporation at room temperature. The resulting pharmaceutical composition is substantially free from ethanol and water, is suitable for oral administration, and contains about 31.82% acetaminophen, 3.82% pseudoephedrine hydrochloride, 1.90% dextromethorphan hydrobromide, 0.48% doxylamine succinate, 58.80% polyethylene glycol 600, and 3.18% polyvinylpyrrolidone.

EXAMPLE IV

Soft Gelatin Capsule Containing A Solubilized Acetaminophen Composition

A gelatin solution is prepared as described in Example II. Using standard encapsulation methodology, this gelatin solution is used to prepare soft gelatin capsules containing approximately 1000 mg of the pharmaceutical composition of Example III. The resulting soft gelatin pharmaceutical capsules are suitable for oral administration.

EXAMPLE V

Solubilized Pharmaceutical Composition

A highly concentrated solution containing acetaminophen in combination with other pharmaceutical actives is prepared from the following ingredients.

| Ingredient | Weight % |
|---|---|
| Acetaminophen | 23.20 |
| Pseudoephedrine Hydrochloride | 2.78 |
| Dextromethorphan Hydrobromide | 1.39 |
| Doxylamine Succinate | 0.58 |
| Polyethylene Glycol 600 | 46.47 |
| Polyvinylpyrrolidone[1] | 1.86 |
| Propylene Glycol | 3.72 |
| Ethanol 95% USP | QS 100 |

[1]Available as Plasdone ® K-29/32 from GAF Chemicals Co.

The acetaminophen, pseudoephedrine hydrochloride, dextromethorphan hydrobromide, doxylamine succinate, polyethylene glycol 600, polyvinylpyrrolidone, propylene glycol, and ethanol are combined in a suitable vessel and mixed at room temperature until a homogeneous solution is formed. Next, the ethanol is removed by rotary evaporation. The resulting pharmaceutical composition is substantially free from ethanol and water, is suitable for oral administration, and contains about 29.00% acetaminophen, 3.48% pseudoephedrine hydrochloride, 1.74% dextromethorphan hydrobromide, 0.72% doxylamine succinate, 58.09% polyethylene glycol 600, and 2.32% polyvinyl-pyrrolidone, and 4.64% propylene glycol.

EXAMPLE VI

Soft Gelatin Capsule Containing a Solubilized Pharmaceutical Composition

A gelatin solution is prepared as describe din Example II. Using standard encapsulation methodology, this gelatin solution is used to prepare soft gelatin capsules containing approximately 1000 mg of the pharmaceutical composition of Example V. The resulting soft gelatin pharmaceutical capsules are suitable for oral administration.

EXAMPLE VII

Solubilized Pharmaceutical Composition

A highly concentrated solution containing acetaminophen in combination with other pharmaceutical actives is prepared from the following ingredients.

| Ingredient | Weight % |
|---|---|
| Acetaminophen | 22.22 |
| Pseudoephedrine Hydrochloride | 2.67 |
| Dextromethorphan Hydrobromide | 0.89 |
| Guaifenesin | 8.89 |
| Polyethylene Glycol 600 | 40.00 |
| Polyvinylpyrrolidone[1] | 1.78 |
| Propylene Glycol | 3.56 |
| Ethanol 95% USP | QS 100 |

[1]Available as Plasdone ® K-29/32 from GAF Chemicals Co.

The acetaminophen, pseudoephedrine hydrochloride, dextromethorphan hydrobromide, guaifenesin, polyethylene glycol 600, polyvinylpyrrolidone, propylene glycol, and ethanol are combined in a suitable vessel and mixed at room temperature until a homogeneous solution is formed. Next, the ethanol is removed by rotary evaporation. The resulting pharmaceutical composition is substantially free from ethanol and water, is suitable for oral administration, and contains about 27.77% acetaminophen, 3.34% pseudoephedrine hydrochloride, 1.11% dextromethorphan hydrobromide, 11.11% guaifenesin, 49.99% polyethylene glycol 600, 2.22% polyvinylpyrrolidone, and 4.45% propylene glycol.

EXAMPLE VIII

Soft Gelatin Capsule Containing a Solubilized Pharmaceutical Composition

A gelatin solution is prepared as describe din Example II. Using standard encapsulation methodology, this gelatin solution is used to prepare soft gelatin capsules containing approximately 1000 mg of the pharmaceutical composition of Example VII. The resulting soft gelatin pharmaceutical capsules are suitable for oral administration.

EXAMPLE IX

Solubilized Pharmaceutical Composition

A highly concentrated solution containing acetaminophen in combination with other pharmaceutical actives is prepared from the following ingredients:

| Ingredient | Weight % |
|---|---|
| Acetaminophen | 25.26 |
| Pseudoephedrine Hydrochloride | 3.03 |
| Dextromethorphan Hydrobromide | 1.52 |
| Chlorpheniramine Maleate | 0.20 |
| Polyethylene Glycol 600 | 43.91 |
| Polyvinylpyrrolidone[1] | 2.02 |
| Propylene Glycol | 4.04 |
| Ethanol 95% USP | QS 100 |

[1]Available as Plasdone ® K-29/32 from GAF Chemicals Co.

The acetaminophen, pseudoephedrine hydrochloride, dextromethorphan hydrobromide, chlorpheniramine maleate, polyethylene glycol 600, polyvinylpyrrolidone, propylene glycol, and ethanol are combined in a suitable vessel and mixed at room temperature until a homogeneous solution is formed. Next, the ethanol is removed by rotary evaporation. The resulting pharmaceutical composition is substantially free from ethanol and water, is suitable for oral administration, and contains about 31.58% acetaminophen, 3.79% pseudoephedrine hydrochloride, 1.90% dextromethorphan hydrobromide, 0.25% chlorpheniramine maleate, 54.90% polyethylene glycol 600, and 2.53% polyvinylpyrrolidone, and 5.05% propylene glycol.

EXAMPLE X

Soft Gelatin Capsule Containing a solubilized Pharmaceutical Composition

A gelatin solution is prepared as describe din Example II. Using standard encapsulation methodology, this gelatin solution is used to prepare soft gelatin capsules containing approximately 1000 mg of the pharmaceutical composition of Example IX. The resulting soft gelatin pharmaceutical capsules are suitable for oral administration.

What is claimed is:

1. A process not requiring the use of heat or surfactants for solubilizing difficulty soluble pharmaceutical actives, comprising the steps of:
    (a) combining and mixing until dissolved
        (i) from about 1% to about 40% of at least one difficulty soluble pharmaceutical active,
        (ii) from about 20% to about 70% of a polyethylene glycol,
        (iii) from about 1% to about 28% of a polyvinylpyrrolidone, and
        (iv) from about 1% to about 50% of a solvent selected from the group consisting of the monohydric alcohols having from 1 to 4 carbon atoms and mixtures thereof,
    wherein the ratio of said polyethylene glycol to said polyvinylpyrrolidone is at least about 2.5:1; and
    (b) evaporating said solvent to obtain a composition containing from about 0.1% to about 6% by weight of said solvent and from about 1.25% to about 50% of said difficulty soluble pharmaceutical active.

2. A process according to claim 1 wherein said solvent is ethanol.

3. A process according to claim 2 wherein said difficulty soluble pharmaceutical active is added in an mount from about 15% to about 35%.

4. A process according to claim 3 wherein said difficulty soluble pharmaceutical active is added in an amount from about 20% to about 30%.

5. A process according to claim 4 wherein said polyethylene glycol is added in an amount from about 30% to about 60% and said polyvinylpyrrolidone is added in an amount from about 1% to about 10%.

6. A process according to claim 5 wherein said polyethylene glycol is added in an amount from about 40% to about 50% and said polyvinylpyrrolidone is added in an amount from about 1% to about 5%.

7. A process according to claim 6 wherein said difficulty soluble pharmaceutical active is selected from the group consisting of acetaminophen, acetylsalicylic acid, ibuprofen, fenbuprofen, fenoprofen, flubiprofen, indomethacin, naproxen, and mixtures thereof.

8. A process according to claim 7 wherein said difficultly soluble pharmaceutical active is acetaminophen.

9. A process according to claim 8 wherein said polyethylene glycol is selected from the group consisting of PEG-6, PEG-8, PEG-9, PEG-10, PEG-12, PEG-14, PEG-16, PEG-18, PEG-20, and mixtures thereof.

10. A process according to claim 9 wherein said polyethylene glycol is PEG-12.

11. A process according to claim 10 wherein said polyvinylpyrrolidone has an average molecular weight of about 9,000 to about 45,000.

12. A process according to claim 11 wherein said polyvinylpyrrolidone has an average molecular weight of about 29,000.

13. A process according to claim 1 which further comprises combining in step (a) from about 0.5% to about 20% of a second pharmaceutical active selected from the group consisting of dextromethorphan hydrobromide, doxyllamine succinate, pseudoephedrine hydrochloride, chlorpheniramine maleate, guaifenesin, triprolidine hydrochloride, diphenhydramine hydrochloride, and mixtures thereof.

14. A process not requiring the use of heat or surfactants for preparing soft gelatin capsules of a highly-concentrated liquid, pharmaceutical composition, comprising the steps of:
    (a) combining and mixing until dissolved
        (i) from about 1% to about 40% of at least one difficulty soluble pharmaceutical active,
        (ii) from about 20% to about 70% of a polyethylene glycol,
        (iii) from about 1% to about 28% of a polyvinylpyrrolidone, and
        (iv) from about 1% to about 50% of a solvent selected from the group consisting of monohydric alcohols having from one to four carbon atoms and mixtures thereof,
    wherein the ratio of said polyethylene glycol to said polyvinylpyrrolidone is at least about 2.5:1;
    (b) evaporating said solvent to obtain a composition containing from about 0.1% to about 6% by weight of said solvent and from about 1.25% to about 50% of said difficultly soluble pharmaceutical active; and
    (c) encapsulating the evaporated composition in a soft gelatin shell.

15. A process according to claim 14 wherein said solvent is ethanol.

16. A process according to claim 15 wherein said difficulty soluble pharmaceutical active is selected from the group consisting of acetaminophen, acetylsalicylic acid, ibuprofen, fenbuprofen, fenoprofen, flurbiprofen, indomethacin, naproxen, and mixtures thereof.

17. A process according to claim 16 which further comprises combining in step (a) from about 0.5% to about 20% of a second pharmaceutical active selected from the group consisting of dextromethorphan hydrobromide, doxylamine succinate, pseudoephedrine hydrochloride, chlorpheniramine maleate, guaifenesin, triprolidine hydrochloride, diphenhydramine hydrochloride, and mixtures thereof.

18. A highly-concentrated liquid, pharmaceutical composition prepared in accordance with the process of claim 1.

19. A highly-concentrated liquid, pharmaceutical composition prepared in accordance with the process of claim 7.

20. A highly-concentrated liquid, pharmaceutical composition prepared in accordance with the process of claim 13.

21. A soft gelatin capsule prepared in accordance with the process of claim 14.

22. A soft gelatin capsule prepared in accordance with the process of claim 16.

23. A soft gelatin capsule prepared in accordance with the process of claim 17.

24. A highly-concentrated liquid, pharmaceutical composition which is substantially free from solvent and surfactants, comprising:
   (a) from about 1.25% to about 50% of at least one difficultly soluble pharmaceutical active;
   (b) from about 25% to about 87.5% of a polyethylene glycol;
   (c) from about 1.25% to about 35% of a polyvinylpyrrolidone; and
   (d) from about 0.1% to about 8% water; wherein the ratio of said polyethylene glycol to said polyvinylpyrrolidone is at least about 2.5:1.

* * * * *